United States Patent
Oh et al.

(10) Patent No.: US 8,107,078 B2
(45) Date of Patent: Jan. 31, 2012

(54) DETECTING DEVICE AND METHOD FOR DETECTING UNEVENNESS OF A GLASS SUBSTRATE

(75) Inventors: Kum-Mi Oh, Seoul (KR); Yong-Won Zeon, Seoul (KR)

(73) Assignee: LG Display Co., Ltd., Seoul (KR)

( * ) Notice: Subject to any disclaimer, the term of this patent is extended or adjusted under 35 U.S.C. 154(b) by 457 days.

(21) Appl. No.: 12/314,699

(22) Filed: Dec. 15, 2008

(65) Prior Publication Data

US 2009/0219531 A1    Sep. 3, 2009

(30) Foreign Application Priority Data

Mar. 3, 2008 (KR) .................. 10-2008-0019513

(51) Int. Cl.
*G01J 4/00* (2006.01)
*G01N 21/00* (2006.01)

(52) U.S. Cl. .............. 356/370; 356/364; 356/237.1; 356/239.1

(58) Field of Classification Search .................. None
See application file for complete search history.

(56) References Cited

U.S. PATENT DOCUMENTS

| | | | | |
|---|---|---|---|---|
| 4,072,422 A * | 2/1978 | Tanaka et al. | | 356/491 |
| 5,311,284 A * | 5/1994 | Nishino | | 356/364 |
| 5,734,158 A * | 3/1998 | Nagashima et al. | | 250/225 |
| 6,636,322 B1 * | 10/2003 | Terashita | | 356/492 |
| 2004/0008297 A1 * | 1/2004 | Ozeki et al. | | 349/74 |
| 2006/0049408 A1 * | 3/2006 | Sohn et al. | | 257/72 |
| 2008/0116928 A1 * | 5/2008 | Kim et al. | | 324/770 |

FOREIGN PATENT DOCUMENTS

| | | | | |
|---|---|---|---|---|
| JP | 08136876 A | * | 5/1996 | |
| JP | 2005242234 A | * | 9/2005 | |
| JP | 2005274173 A | * | 10/2005 | |
| JP | 2007240210 A | * | 9/2007 | |

* cited by examiner

*Primary Examiner* — Gordon Stock, Jr.
(74) *Attorney, Agent, or Firm* — McKenna Long & Aldridge LLP

(57) ABSTRACT

A detecting device of unevenness of a glass substrate includes a light source emitting a light; a polarizer polarizing the light; a standard cell including opposing outer surfaces, the glass substrate attached to one of the opposing outer surfaces, the polarized light passing through the standard cell and the glass substrate; an analyzer detecting and analyzing the light passing through the standard cell and the glass substrate.

17 Claims, 10 Drawing Sheets

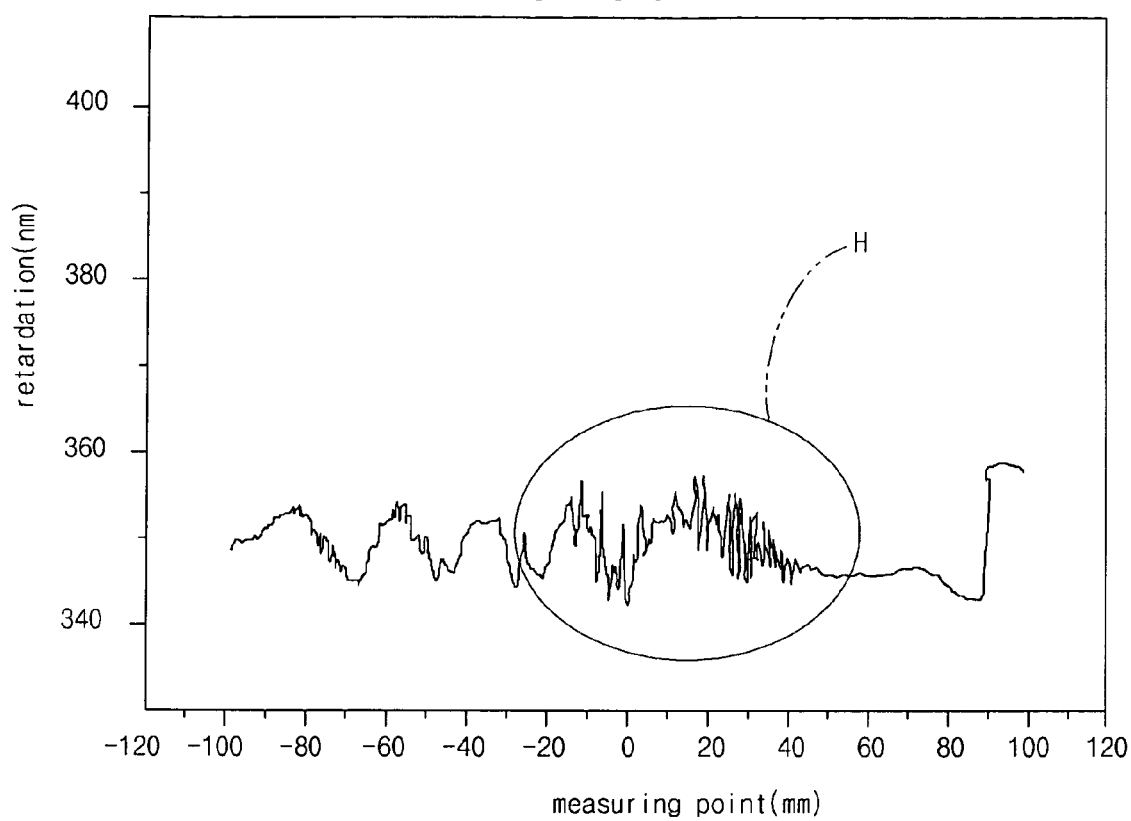

DETECTING DEVICE AND METHOD FOR DETECTING UNEVENNESS OF A GLASS SUBSTRATE

The present invention claims the benefit of Korean Patent Application No. 2008-0019513, filed in Korea on Mar. 3, 2008, which is hereby incorporated by reference for all purposes as if fully set forth herein.

BACKGROUND OF THE INVENTION

1. Field of the Invention

The present invention relates to detecting device and method of unevenness of a glass substrate.

2. Discussion of the Related Art

Until recently, display devices have typically used cathode-ray tubes (CRTs). Presently, many efforts and studies are being made to develop various types of flat panel displays, such as liquid crystal display (LCD) devices, plasma display panels (PDPs), field emission displays, and electro-luminescence displays (ELDs), as a substitute for CRTs. Of these flat panel displays, LCD devices have many advantages, such as high resolution, light weight, thin profile, compact size, and low voltage power supply requirements.

In general, an LCD device includes two substrates that are spaced apart and face each other with a liquid crystal material interposed between the two substrates. The two substrates include electrodes that face each other such that a voltage applied between the electrodes induces an electric field across the liquid crystal material. Alignment of the liquid crystal molecules in the liquid crystal material changes in accordance with the intensity of the induced electric field into the direction of the induced electric field, thereby changing the light transmissivity of the LCD device. Thus, LCD devices display images by varying the intensity of the induced electric field.

FIG. 1 is a cross-sectional view of a LCD device.

Referring to FIG. 1, the LCD device 95 includes a liquid crystal panel 30 including an array substrate 10, a color filter substrate 5, and a liquid crystal layer 15 between the array and color filter substrates 10 and 5 and having a cell gap d, and a backlight unit 90.

The array substrate 10 includes gate and data lines crossing each other on a first glass substrate 2 to define a pixel region. In the pixel region P, a thin film transistor T in a switching region S and a pixel electrode 70 are formed. The thin film transistor T includes a gate electrode 25, a semiconductor layer 40 and source and drain electrodes 32 and 34. The pixel electrode 70 is connected to the drain electrode 34 through a drain contact hole CH1. A gate insulating layer 45 is on the gate electrode 25. A passivation layer 55 is on the thin film transistor T and has the drain contact hole CH1. A first alignment layer 76 is on the pixel electrode 70.

The color filter substrate 5 includes a black matrix 12 on a second glass substrate 1 and a color filter layer 16 including red (R), green (G) and blue color filter patterns 16a and 16b in the respective pixel regions P. A common electrode 80 is on the color filter layer 16. A second alignment layer 75 is on the common electrode 80.

The first and second glass substrates 2 and 1 usually have a thickness of about 1.1 mm. Recently, the glass substrate having a thickness of about 0.7 mm is used. The glass substrate is usually manufactured by a floating or fusion method.

However, the glass substrate may have unevenness on a surface thereof due to a manufacturing process. The unevenness may be referred to as a Uneri. A stripe pattern due to the unevenness occurs at the surface.

FIG. 2A is a plan view illustrating a mother glass substrate having unevenness, and FIG. 2B is a cross-sectional view illustrating a line II-II of FIG. 2A.

Referring to FIGS. 2A and 2B, the mother glass substrate 100 includes a plurality of portions F. Each portion F may be the first glass substrate 2 or the second glass substrate 1 of the liquid crystal panel (30 of FIG. 1) after a cutting process. In other words, deposition process, exposure process, developing process, etching process and the like are performed on the mother glass substrate 100 for the array substrate (10 of FIG. 1) and on the mother glass substrate 100 for the color filter substrate (5 of FIG. 1), the two mother glass substrates are attached and cut into portions F, and the liquid crystal panels are manufactured.

The mother glass substrate 100 has unevenness 110 on a surface of the mother glass substrate 100. The unevenness 110 is a defect caused in manufacturing the mother glass substrate 100. Protrusions of the unevenness 110 have a stripe pattern. The unevenness 110 may occur at at least one surface of the mother glass substrate 100. The protrusion of the unevenness 110 may have various shapes, for example, a triangular shape, a half round shape and the like. The stripes of the unevenness may be at the overall surface of the mother glass substrate 100.

The protrusion may have a height h in a large range at the surface of the mother glass substrate 100 having a predetermined thickness t. However, even though the height h of the protrusion is about 30 nm, and in particular, very small, about 10 nm, stains of a stripe pattern occur in an display inspection process due to the unevenness, and display quality is thus degraded. The unevenness defect of the mother glass substrate 100 exists in the initial step of manufacturing an LCD device, and the mother glass substrate 100 accounts for a large amount of the production cost of the LCD device. Accordingly, the production efficiency is reduced. Therefore, a system for early detecting the unevenness of the mother glass substrate 100 is needed. However, it is difficult to detect the unevenness because the height of the unevenness is very small.

In the related art, there have been a contact method and a non-contact method to detect unevenness of s mother glass substrates. A waviness method is used as the contact method. The waviness method has a good reliability, but it may cause defects in the mother glass substrate 100 since the method requires cutting the mother glass substrate 100 and wears away the mother glass substrate 100 in the detecting process.

An optical method employing a Xe lamp is used as the non-contact method. Since the optical method is a nondestructive detecting method, it is easy to detect the unevenness of the mother glass substrate 100.

FIG. 3 is a view illustrating a detecting device of unevenness of a glass substrate according to the related art.

Referring to FIG. 3, the detecting device 150 includes a Xe lamp 155, a screen 170 spaced apart from the Xe lamp 155, and a stage 165 between the Xe lamp 155 and the screen 170.

The device 150 uses a principle that the Xe lamp 155 emits a light and the light passing through the glass substrate 160 produces images on the screen 170.

In a state that a thickness surface T of the glass substrate 160 faces the Xe lamp 155, the light does not pass through the glass substrate 160 and any image is not produced on the screen 170. While the glass substrate 160 is rotated by the stage 165 in a clockwise or counterclockwise direction, the light emitted from the Xe lamp 155 passes through the glass substrate 160, and images are thus produced on the screen 170. Whether or not the unevenness exists is determined according to relationship of change of the rotating angle and the image produced on the screen 170. In other words, the detecting method uses difference of transmissivity according to the change of the rotating angle.

However, the detecting method is conducted by a human's eyes, and thus, the determination depends on a detecting worker and there is a deviation in determining the unevenness. Further, it is difficult to database detecting results. Accordingly, reliability of the related art method is reduced.

SUMMARY OF THE INVENTION

Accordingly, the present invention is directed to a detecting device and a method of detecting unevenness of a glass substrate that substantially obviates one or more of the problems due to limitations and disadvantages of the related art.

An advantage of the present invention is to provide a detecting device and a method of detecting unevenness of a glass substrate for a liquid crystal display device that can improve reliability.

Additional features and advantages of the present invention will be set forth in the description which follows, and in part will be apparent from the description, or may be learned by practice of the invention. These and other advantages of the invention will be realized and attained by the structure particularly pointed out in the written description and claims hereof as well as the appended drawings.

To achieve these and other advantages and in accordance with the purpose of the present invention, as embodied and broadly described herein, a detecting device of unevenness of a glass substrate includes a light source emitting a light; a polarizer polarizing the light; a standard cell including opposing outer surfaces, the glass substrate attached to one of the opposing outer surfaces, the polarized light passing through the standard cell and the glass substrate; an analyzer detecting and analyzing the light passing through the standard cell and the glass substrate.

In another aspect, a detecting method of unevenness of a glass substrate includes emitting a light from a light source; polarizing the light through a polarizer; passing the polarized light through a standard cell and the glass substrate, the glass substrate attached to one of opposing outer surfaces of the standard cell; and detecting and analyzing the light passing through the standard cell and the glass substrate.

In another aspect, a method of manufacturing a liquid crystal display device includes providing two glass substrates that are spaced apart and face each other with a liquid crystal material interposed between the two glass substrates, wherein at least one of the glass substrates is subjected to a method of detecting unevenness including the steps of: emitting a light from a light source; polarizing the light through a polarizer; passing the polarized light through a standard cell and the glass substrate, the glass substrate attached to one of opposing outer surfaces of the standard cell; and detecting and analyzing the light passing through the standard cell and the glass substrate.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIGS. 10A and 10B are graphs illustrating retardation waveforms detected for the two substrates of FIGS. 9A and 9B, respectively, by the detecting device according to the embodiment of the present invention.

DETAILED DESCRIPTION OF THE ILLUSTRATED EMBODIMENTS

Reference will now be made in detail to illustrated embodiments of the present invention, which are illustrated in the accompanying drawings.

Figure 1:
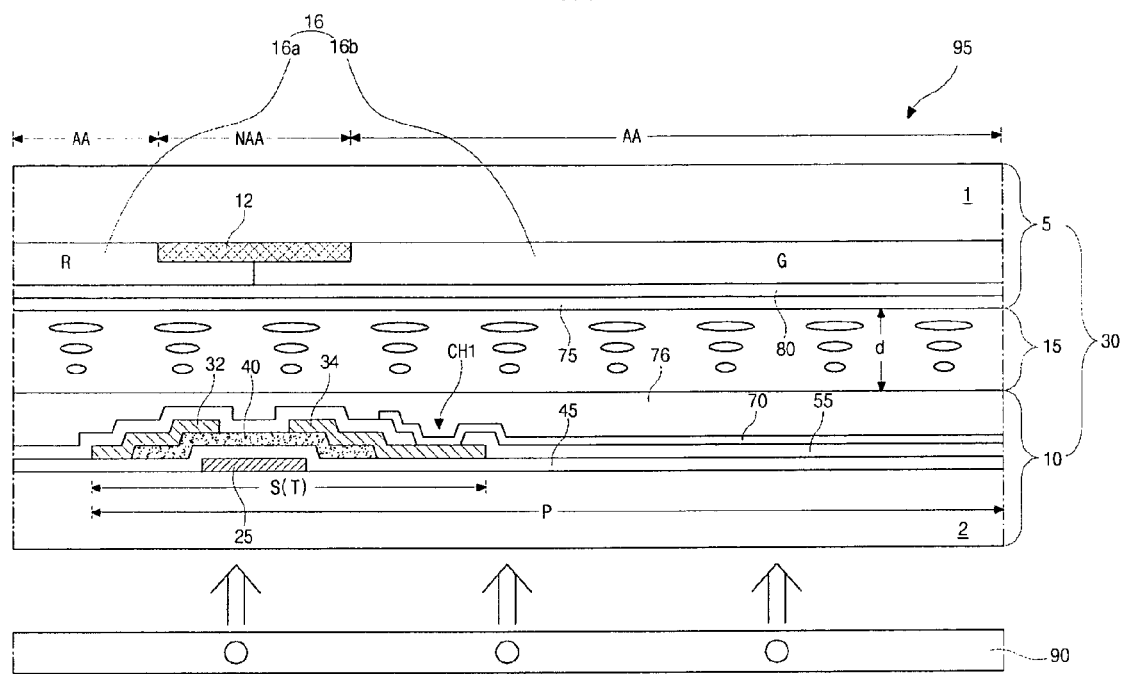
FIG. 1 is a cross-sectional view of an LCD device.
Figure 2A:
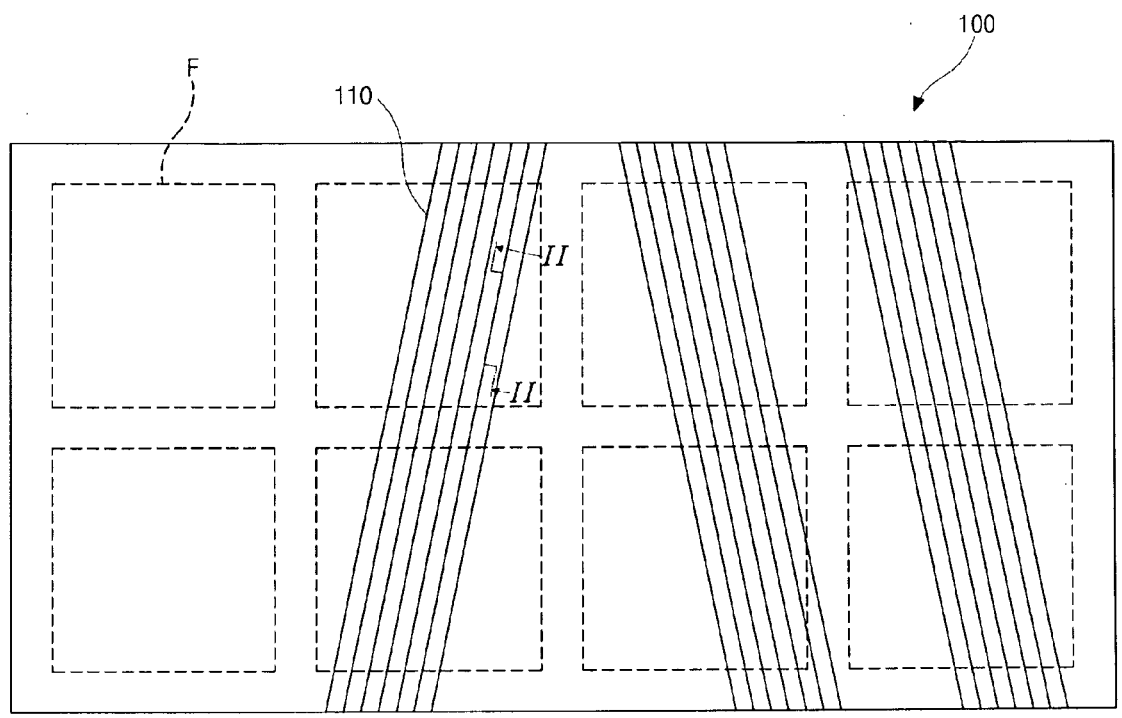
FIG. 2A is a plan view illustrating a mother glass substrate having unevenness.
Figure 2B:
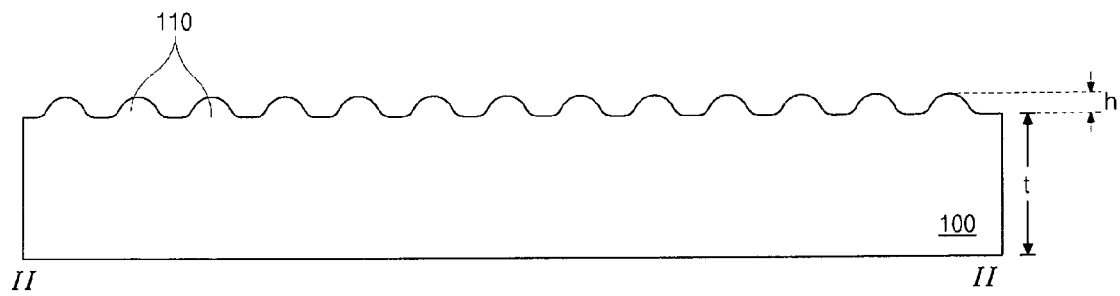
FIG. 2B is a cross-sectional view illustrating a line II-II of FIG. 2A.
Figure 3:
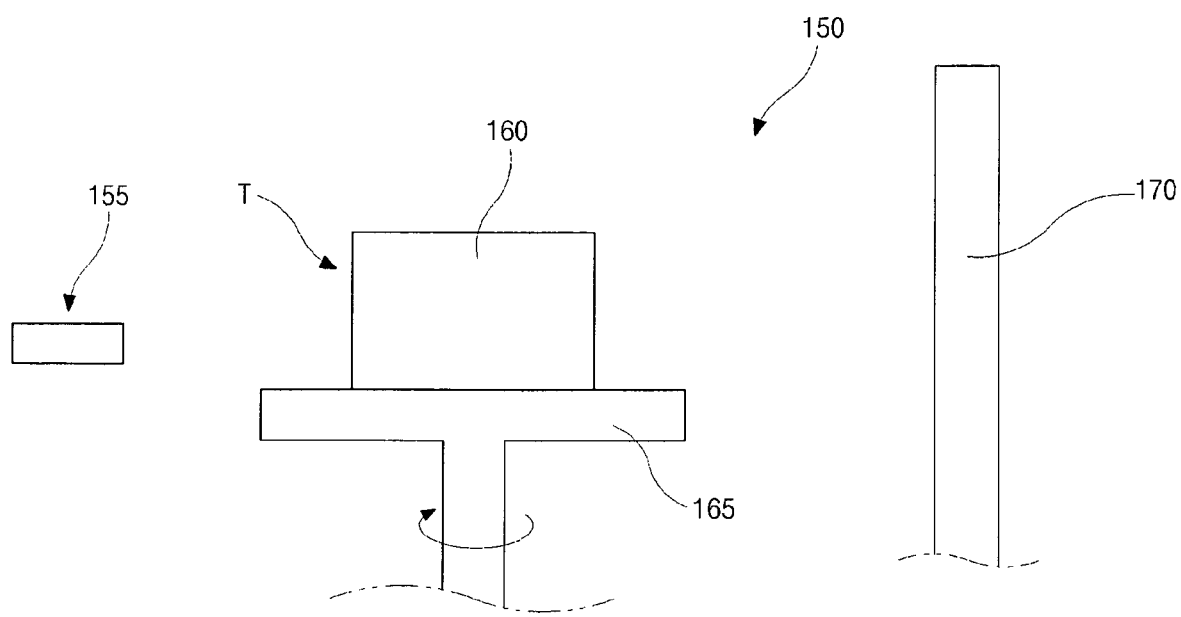
FIG. 3 is a view illustrating a detecting device of unevenness of a glass substrate according to the related art.
Figure 4:
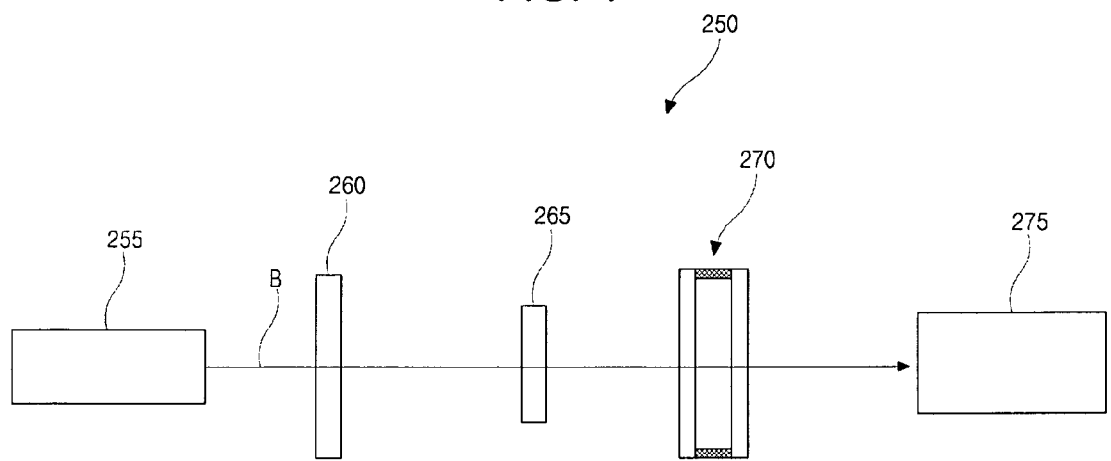
FIG. 4 is a view illustrating a detecting device of unevenness of a glass substrate according to an embodiment of the present invention.

FIG. 4 is a view illustrating a detecting device of unevenness of a glass substrate according to an embodiment of the present invention.

Referring to FIG. 4, the detecting device 250 includes a light source 255, a polarizer 260, a standard cell 270, and an analyzer 275.

The light source 255 may be a laser, for example, a gas laser, a solid laser, a liquid laser, a semiconductor laser or the like. Accordingly, the detecting device 250 is a non-contact type detecting device.

A size of the laser beam B, for example, a spot size may be an important factor in the device 250. For example, the spot size may be greater than 0 mm and smaller than or equal to about 5 mm. In a particular embodiment, the spot size is about 1 mm.

The polarizer 260 transmits a light having an optical axis identical to a polarizing axis of the polarizer 260 and blocks or reflects a light having an optical axis different from the polarizing axis.

The glass substrate 265 is a substrate to detect whether or not unevenness exists on the glass substrate 265. The glass substrate 265 may be a mother glass substrate or a sample glass substrate which may be a sample portion of the mother glass substrate. The unevenness may exist substantially all over the mother glass substrate, and the sample glass substrate prepared by cutting the mother glass substrate may be used in the detecting process.

The polarizer 260, the glass substrate 265, and the standard cell 270 may be in parallel to one another. The glass substrate 265 may face one of outer surfaces of the standard cell 270, for example, be located between the polarizer 260 and the standard cell 270 or between the standard cell 270 and the analyzer 275.

The standard cell 270 may include first and second substrates and a liquid crystal layer between the first and second substrates. The liquid crystal layer is an anisotropic material having both an ordinary refractive index and an extraordinary refractive index.

The detecting device 250 uses a birefringence property of the standard cell 270. The glass substrate 265 may move relatively to the standard cell 270 and be attached to and detached from the standard cell 270. In a detecting process, the glass substrate 265 may be attached to the standard cell 270 and scanned by the laser beam B several times in order to increase accuracy of detecting the unevenness. In the scanning process, the light source 255 may move relatively to the glass substrate 265. For example, the glass substrate 265 attached to the standard cell 270 may move in parallel to a plane of the glass substrate 265, or the light source 255 may move in parallel to the plane of the glass substrate 265.

Figure 5:
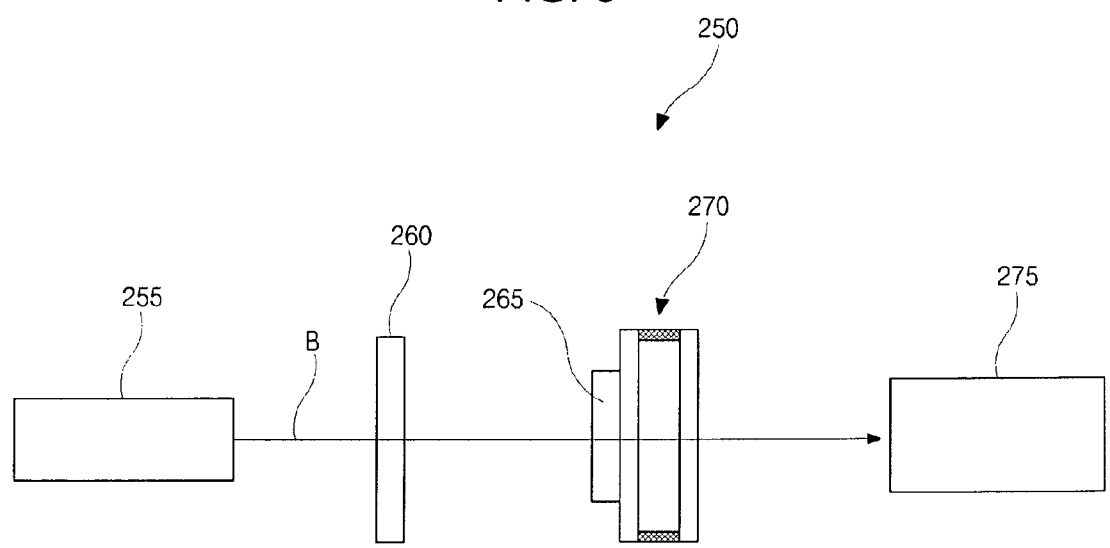
FIG. 5 is a view illustrating the detecting device in a detecting process according to the embodiment of the present invention.

FIG. 5 is a view illustrating the detecting device in a detecting process according to the embodiment of the present invention.

Referring to FIG. 5, the glass substrate 265 may be moved relative to and attached to the standard cell 270. Then, the light source 255 may scan in a direction parallel to the plane of the glass substrate 265 and emit laser beams B to the polarizer 260, and linearly polarized laser beams B having an optical axis of the polarizing axis of the polarizer 260 are produced. The linearly polarized laser beams B pass through the glass substrate 265 and the standard cell 270 and are incident on the analyzer 275. The analyzer 275 receives the laser beams B in the scanning direction and detects an optical property, for example, retardation values in the scanning direction of a combination of the glass substrate 265 and the standard cell 270. The retardation value may be expressed by a formula, $d*\Delta n$ (wherein d is a thickness, and $\Delta n$ is a difference of an ordinary refractive index and an extraordinary refractive index).

A storing portion may be included in the detecting device 250. The storing portion stores and databases the detected optical property of the combination of the glass substrate 265 and the standard cell 270. The storing portion may be installed in the analyzer 275 or outside the analyzer 275.

Figure 6:
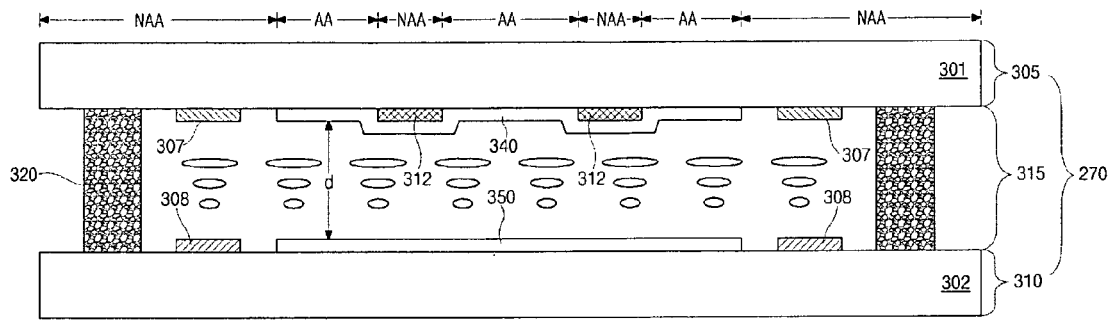
FIG. 6 is a cross-sectional view illustrating the standard cell of the detecting device according to the embodiment of the present invention.

FIG. 6 is a cross-sectional view illustrating the standard cell of the detecting device according to the embodiment of the present invention.

Referring to FIG. 6, the standard cell 270 includes first and second substrates 305 and 310 and a liquid crystal layer 315 between the first and second substrates 305 and 310. A seal pattern 320 is formed in a peripheral region of the first and second substrates 305 and 310 and attaches the first and second substrates 305 and 310. The standard cell 270 may include an active region AA and a non-active region NAA.

The first substrate 305 includes a plurality of first align keys 307 on the peripheral region of a first glass substrate 301 inside the seal pattern 320. A black matrix 312 may be on the non-active region NAA of the first glass substrate 301. A first transparent electrode 340 may be on the first glass substrate 301 having the black matrix 312. The first transparent electrode 340 may be both on the active and non-active regions AA and NAA.

The second substrate 310 includes a plurality of second align keys 308 on the peripheral region of a second glass substrate 302. The second align keys 308 correspond in position to the first align keys 307. A second transparent electrode 350 may be on the second glass substrate 302.

The first and second substrates 305 and 310 are attached using the first and second align keys. The first transparent electrode 340 may be formed on an outer surface of the first glass substrate 301. The second transparent electrode 350 may be formed on an outer surface of the second glass substrate 302. Even though not in the drawings, spacers may be located between the first and second substrates 305 and 310 to maintain a cell gap d. The spacers may be ball spacers or columnar spacers. The standard cell 270 may be modified with other structures.

Figure 7:
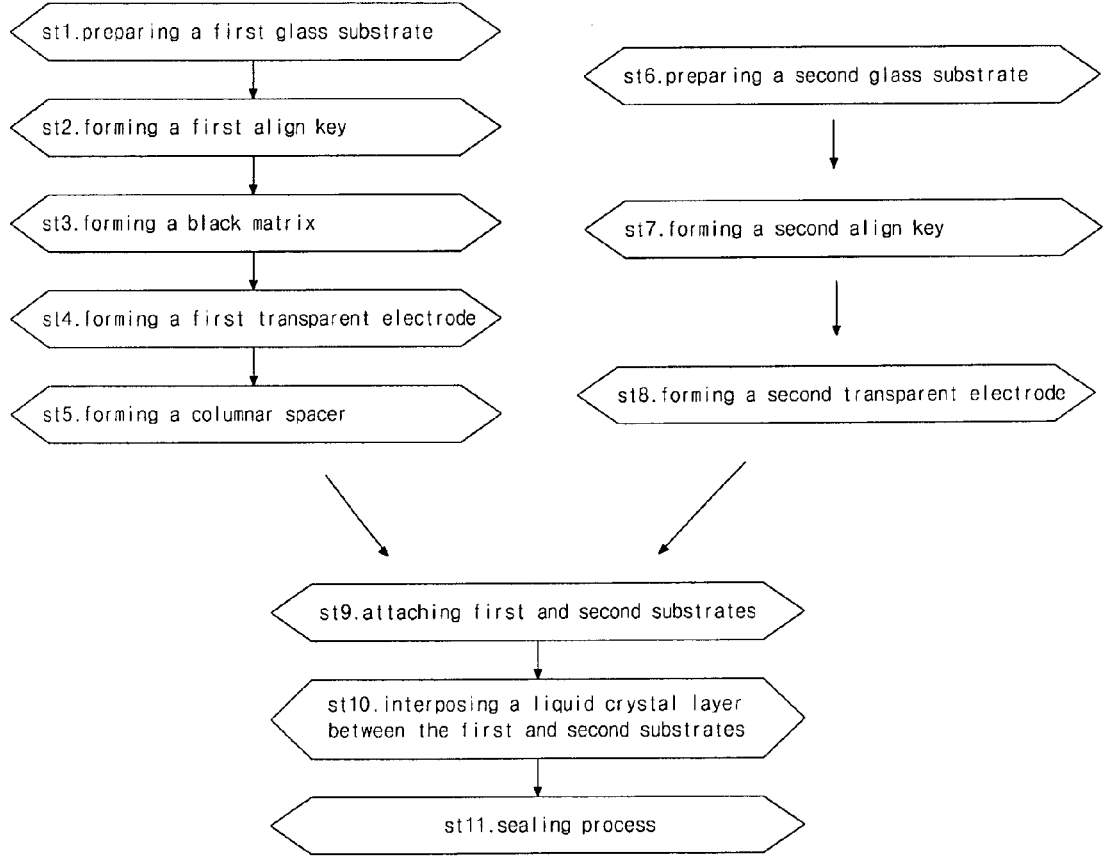
FIG. 7 is a flow chart illustrating manufacturing the standard cell of FIG. 6.

FIG. 7 is a flow chart illustrating manufacturing the standard cell of FIG. 6.

Referring to FIG. 7, in a first step st1, the first glass substrate (301 of FIG. 6) is prepared. Then, in a second step st2, the first align key (307 of FIG. 6) is formed on the first glass substrate. Then, in a third step st3, the black matrix (312 of FIG. 6) is formed on the first glass substrate. Then, in a fourth step st4, the first transparent electrode (340 of FIG. 6) is formed on the first glass substrate having the black matrix. Then, in a fifth step st5, the columnar spacer is formed on the first transparent electrode. Through the aforementioned processes, the first substrate (305 of FIG. 6) is manufactured.

In a sixth step st6, the second glass substrate (302 of FIG. 6) is prepared. Then, in a seventh step st7, the second align key (308 of FIG. 6) is formed on the second glass substrate. Then, in a eighth step st8, the second transparent electrode (350 of FIG. 6) is formed on the second glass substrate. Through the aforementioned processes, the second substrate (310 of FIG. 6) is manufactured.

The first to fifth steps st1 to st5 may be performed separately from the sixth to eighth steps.

In a ninth step st9, the first and second substrates are aligned using the first and second align keys and attached to each other using the seal pattern (320 of FIG. 6). Then, in a tenth step st10, the liquid crystal layer is interposed between the first and second substrates. Then, in an eleventh step st11, a sealing process is performed. Through the first to eleventh processes, the standard cell (270 of FIG. 6) can be manufactured.

Figure 8A:
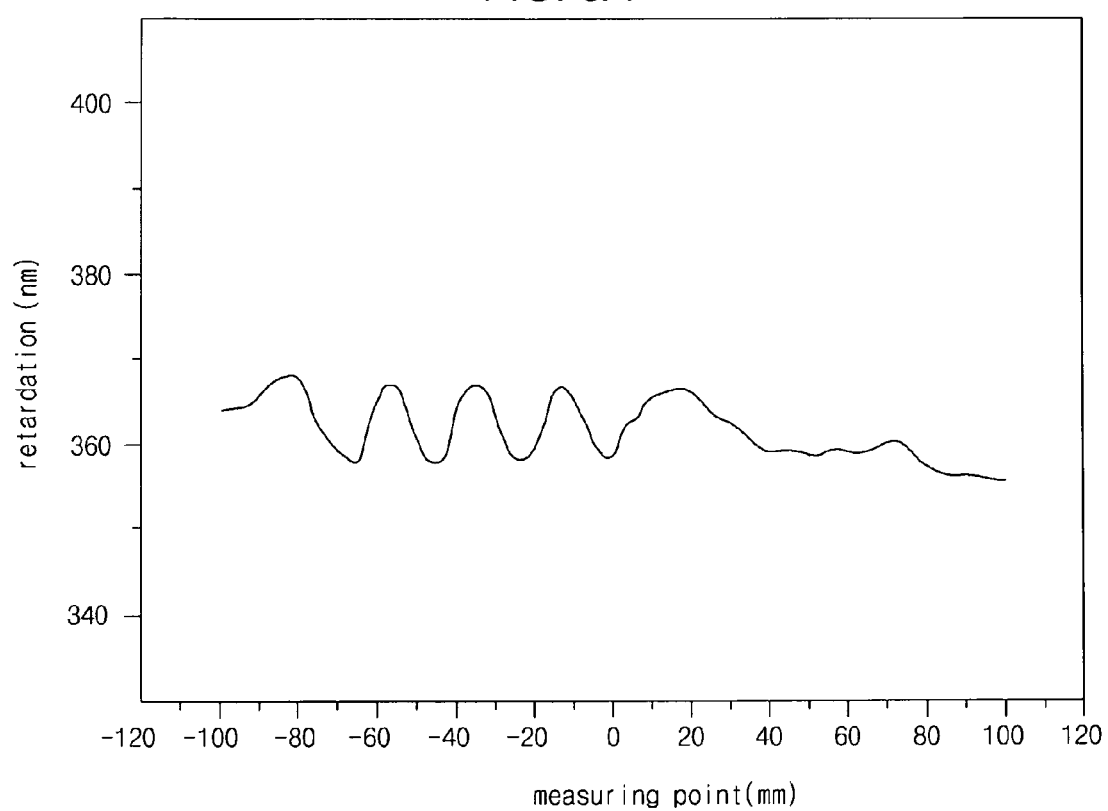
FIG. 8A is a graph illustrating a standard retardation waveform of retardation values of the standard cell according to the embodiment of the present invention.

FIG. 8A is a graph illustrating a standard retardation waveform of retardation values of the standard cell according to the embodiment of the present invention.

In FIG. 8A, the retardation values are measured in a predetermined direction. For example, the predetermined direction may be in an x direction on a plane of the standard cell parallel to a ground. A measuring point, "0" is a reference measuring point, negative measuring points are located in the negative x direction, and positive measuring points are located in the positive x direction. For example, the retardation values of the standard cell (270 of FIG. 5) may be measured without the glass substrate (265 of FIG. 5) by the analyzer (275 of FIG. 5).

The standard retardation waveform may substantially have a sine waveform shape due to interference of the black matrix (312 of FIG. 6) of the standard cell.

The standard retardation waveform is compared with a retardation waveform of a combination of the glass substrate and the standard cell. According to the comparison, whether or not the glass substrate has unevenness is determined.

The first and second glass substrates having no unevenness may be used for the standard cell. Alternatively, both the first and second glass substrates having unevenness may be used for the standard cell. When the unevenness exists in both the first and second glass substrates, the standard cell may be manufactured to have predetermined conditions.

Figure 8B:
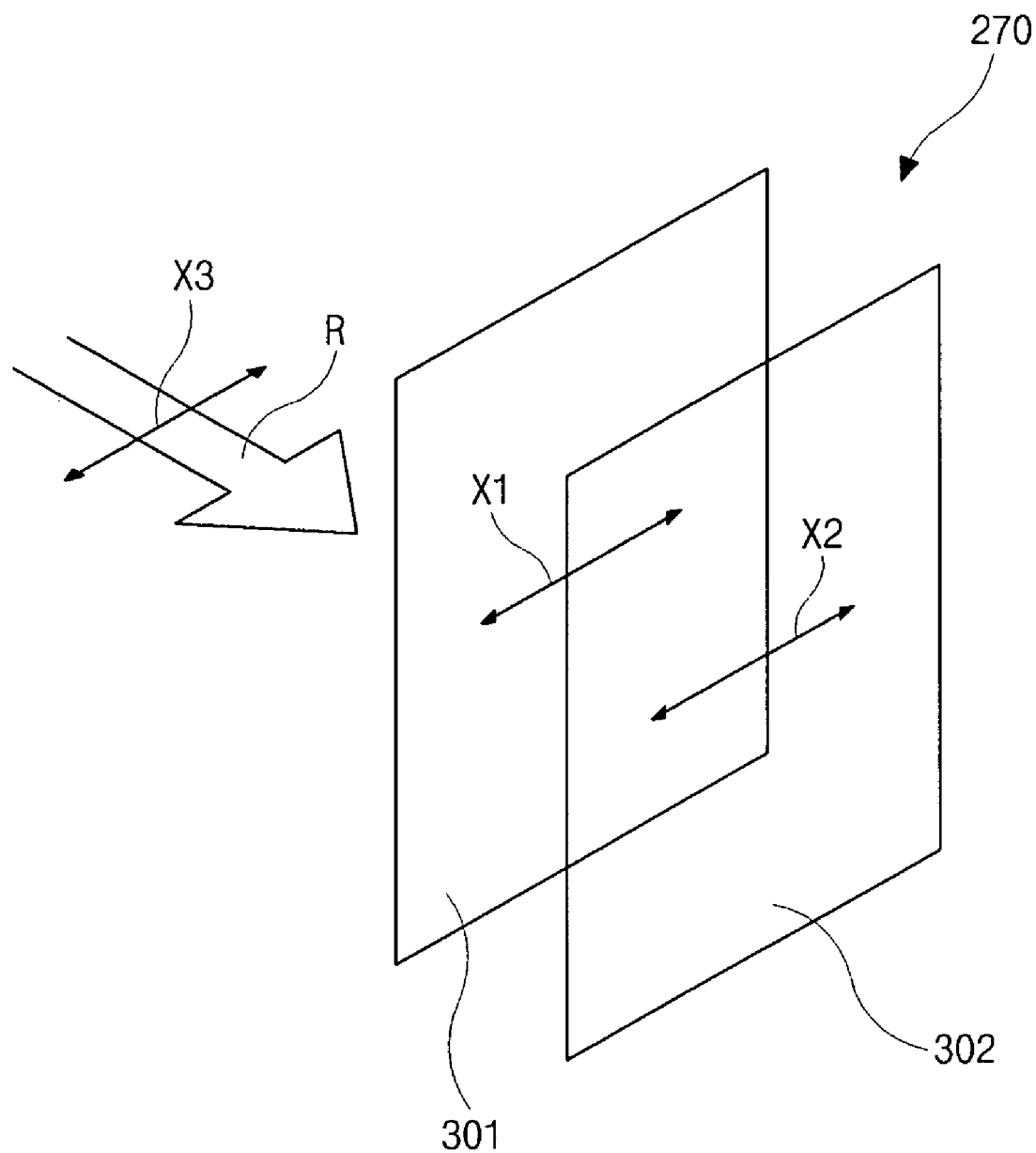
FIG. 8B is a view illustrating the standard cell including the first and second glass substrates having unevenness according to the embodiment of the present invention.

FIG. 8B is a view illustrating the standard cell including the first and second glass substrates having unevenness according to the embodiment of the present invention.

Referring to FIG. 8B, when the first and second glass substrates 301 and 302 having unevenness are used for the standard cell 270, the first and second glass substrates 301 and 302 are arranged such that a first direction X1 of stripes of the unevenness of the first glass substrate 301 may be substantially parallel to a second direction X2 of stripes of the unevenness of the second glass substrate 302. An optical method using a Xe lamp or the detecting device according to the embodiment may be used to check whether or not the first and second directions X1 and X2 are parallel to each other.

When the standard cell 270 including the first and second glass substrates 301 and 302 having the unevenness is used in the detecting device, a scanning direction X3 of the laser beam R is parallel to the first and second directions X1 and X2. In other words, when the scanning direction X3 of the laser beam R is perpendicular to the first and second directions X1 and X2, an effect due to the unevenness of the first and second glass substrate 301 and 302 is revealed. Accordingly, to eliminate the effect due to the unevenness in the detecting process, the scanning direction X3 of the laser beam R is parallel to the first and second directions X1 and X2. Accordingly, the standard cell 270 may have substantially the same optical property, such as retardation values, in the scanning direction X3 as the standard cell including first and second glass substrates having no unevenness.

Figure 9A:
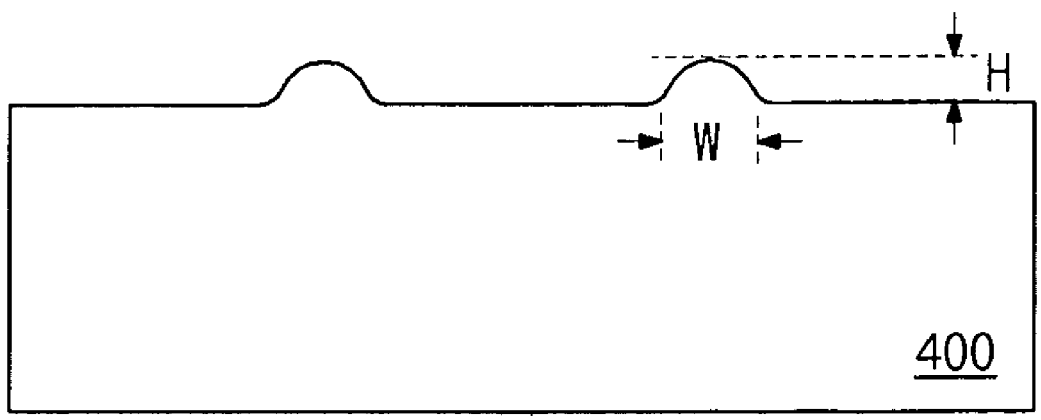
FIGS. 9A and 9B are cross-sectional views illustrating two substrates having different types of unevenness, respectively.
Figure 9B:
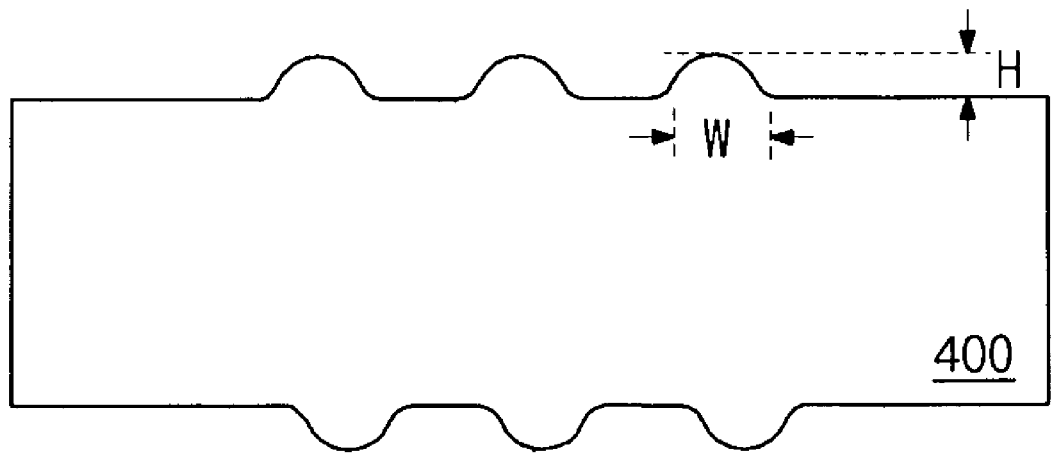
Figure 10B:
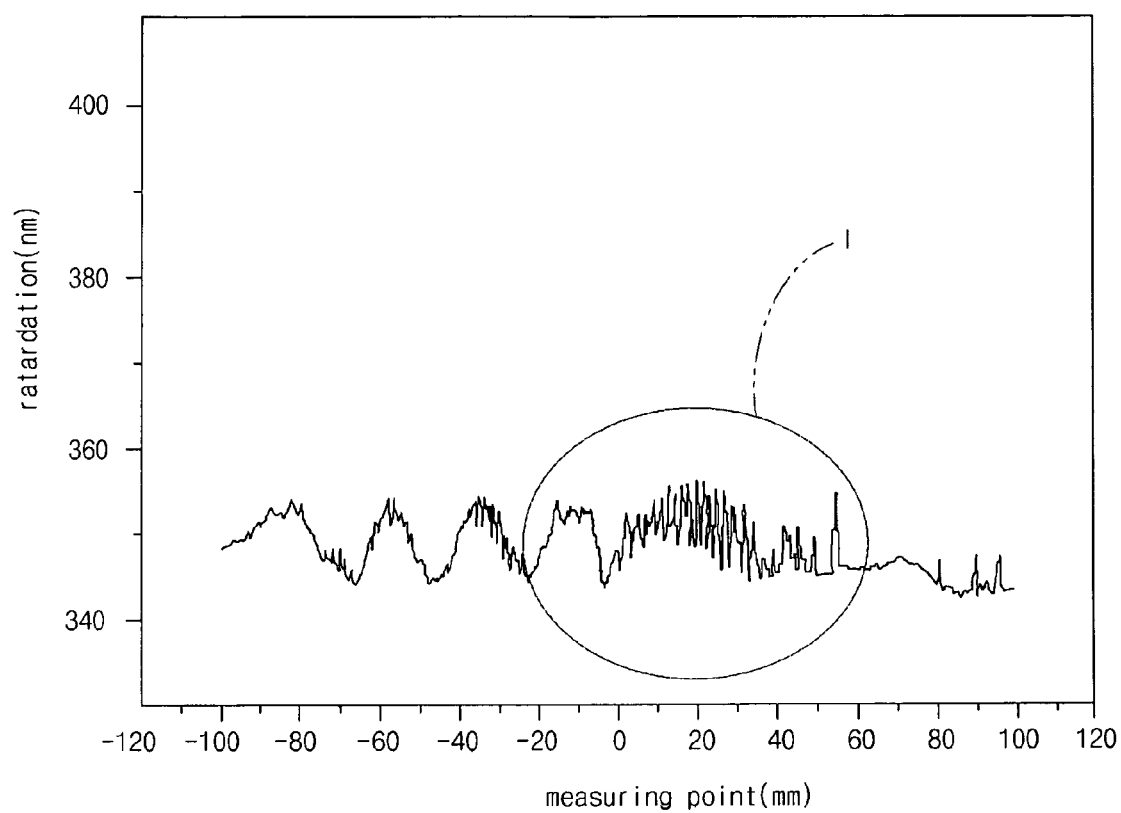

FIGS. 9A and 9B are cross-sectional views illustrating two substrates having different types of unevenness, respectively, and FIGS. 10A and 10B are graphs illustrating retardation waveforms detected for the two substrates of FIGS. 9A and 9B, respectively, by the detecting device according to the embodiment of the present invention.

The unevenness of FIG. 9A may be referred to as a streak type unevenness, and the unevenness of FIG. 9B may be referred to as a cord type unevenness. In the streak type unevenness of FIG. 9A, a surface of the glass substrate 400 protrudes. In the cord type unevenness of 9B, both surfaces of the glass substrate 400 protrude.

The retardation waveforms of FIGS. 10A and 10B corresponding to the streak and cord type unevennesses, respectively, are different from the reference retardation waveform of FIG. 8A. For example, the retardation waveforms of FIGS. 10A and 10B have a shape in a position range of about −100 mm to −20 mm similar to the reference retardation waveform, but rapidly changes in amplitude in a position range (H of FIG. 10A and I of FIG. 10B) of about −20 mm to about +40. In other words, such the rapid change of amplitude shows the glass substrates 400 have unevennesses having a low height.

By detecting and analyzing the retardation waveform of the combination of the glass substrate using the analyzer (275 of FIG. 5), whether or not the glass substrate has unevenness and what type of unevenness the glass substrate has can be determined.

In the streak type unevenness of 9A, the protrusion may have a height, h, of about 10 nm to 20 nm and a width, w, of about 10 nm to 20 nm. In the cord type unevenness of 9B, the protrusion may have a height up to about 10 nm and a width up to about 5 nm. The detecting device according to the embodiment of the present invention can detect such the small-sized streak and cord type unevenness. Further, the detecting device can detect the streak type unevenness having a height less than about 10 nm and a width less than 10 nm and the cord type unevenness having a height less than 5 nm and a width less than 5 nm.

As described above, the detecting device according to the embodiment of the present invention can easily detect whether the glass substrate has unevenness. Further, the detecting results can be databased, and reliability can thus increase.

After the inspection of detecting unevenness of the glass substrates, for example, processes of manufacturing the array substrate or the color filter substrate for the LCD device are performed by forming thin films on the glass substrate passing the inspection. For example, on a first glass substrate including a plurality of portions, thin films for the array substrate are formed in each of the plurality of portions. On a second glass substrate including the plurality of portions, thin films for the color filter substrate are formed in each of the plurality portions. Then, the first and second glass substrates are aligned and attached, then the attached first and second substrates are cut by each of the plurality of portions, and thus, a plurality of liquid crystal panels each including the array substrate and the color filter substrate are manufactured. The liquid crystal panel includes a liquid crystal layer between the array and color filter substrates.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A detecting device of unevenness of a glass substrate, comprising:
   a light source emitting a light;
   a polarizer polarizing the light;
   a standard cell providing reference retardation values and including first and second substrates, a liquid crystal layer between the first and second substrates, and a seal pattern in a peripheral region of the first and second substrates and attaching the first and second substrates;
   a glass substrate disposed between the polarizer and the standard cell, wherein the polarized light passes through the standard cell after passing through the glass substrate;
   an analyzer detecting and analyzing the polarized light passing through the glass substrate and the standard cell.

2. The device according to claim 1, wherein the light source is a laser emitting a laser beam, and the laser beam has a spot size of greater than 0 mm and smaller than or equal to about 5 mm.

3. The device according to claim 1, wherein the light source moves in a predetermined direction relatively to the standard cell and the glass substrate to scan the glass substrate.

4. The device according to claim 1, wherein the standard cell further includes a spacer maintaining a cell gap between the first and second substrates, and wherein the first substrate includes a first glass substrate, a plurality of first align keys in the peripheral region of an inner surface of the first glass substrate, and a black matrix on the inner surface of the first glass substrate.

5. The device according to claim 3, wherein the analyzer detects retardation values of a combination of the standard cell and the glass substrate in the predetermined direction and compares the retardation values with reference retardation values of the standard cell in the predetermined direction.

6. The device according to claim 4, wherein a first electrode is on an outer surface of the first glass substrate or on the black matrix.

7. The device according to claim 4, wherein the second substrate includes a second glass substrate, and a plurality of second align keys on an inner surface of the second glass substrate and corresponding to the plurality of first align keys.

8. The device according to claim 7, wherein a second electrode is on an outer surface of the second glass substrate or on the inner surface of the second glass substrate.

9. A method of detecting unevenness of a glass substrate, comprising:
    emitting a light from a light source;
    polarizing the light through a polarizer;
    passing the polarized light through a standard cell after passing through a glass substrate, the glass substrate disposed between the polarizer and the standard cell; and
    detecting and analyzing the polarized light passing through the glass substrate and the standard cell, and wherein the standard cell provides reference retardation values and includes first and second substrates, a liquid crystal layer between the first and second substrates, and a seal pattern in a peripheral region of the first and second substrates and attaching the first and second substrates.

10. The method according to claim 9, wherein the light is a laser beam, and the laser beam has a spot size of greater than 0 mm and smaller than or equal to about 5 mm.

11. The method according to claim 9, further comprising moving the light source in a predetermined direction relatively to the standard cell and the glass substrate to scan the glass substrate.

12. The method according to claim 9, wherein the standard cell further includes a spacer maintaining a cell gap between the first and second substrates, and wherein the first substrate includes a first glass substrate, a plurality of first align keys in the peripheral region of an inner surface of the first glass substrate, and a black matrix on the inner surface of the first glass substrate.

13. The method according to claim 11, wherein detecting and analyzing the light includes detecting retardation values of a combination of the standard cell and the glass substrate in the predetermined direction and comparing the retardation values with the reference retardation values of the standard cell in the predetermined direction.

14. The method according to claim 12, wherein a first electrode is on an outer surface of the first glass substrate or on the black matrix.

15. The method according to claim 12, wherein the second substrate includes a second glass substrate, and a plurality of second align keys on an inner surface of the second glass substrate and corresponding to the plurality of first align keys.

16. The method according to claim 15, wherein a second electrode is on an outer surface of the second glass substrate or on the inner surface of the second glass substrate.

17. A method of manufacturing a liquid crystal display device comprising providing two glass substrates that are spaced apart and face each other with a liquid crystal material interposed between the two glass substrates, wherein at least one of the glass substrates is subjected to a method of detecting unevenness including the steps of:
    emitting a light from a light source;
    polarizing the light through a polarizer;
    passing the polarized light through a standard cell after passing through a glass substrate, the glass substrate disposed between the polarizer and the standard cell; and
    detecting and analyzing the polarized light passing through the glass substrate and the standard cell, and wherein the standard cell provides reference retardation values and includes first and second substrates, a liquid crystal layer between the first and second substrates, and a seal pattern in a peripheral region of the first and second substrates and attaching the first and second substrates.

* * * * *